United States Patent [19]

Jackson

[11] Patent Number: 4,966,155
[45] Date of Patent: Oct. 30, 1990

[54] APPARATUS FOR MONITORING PHYSIOLOGICAL PARAMETERS

[75] Inventor: John Jackson, Lesmahagow, Scotland

[73] Assignee: The University of Strathclyde, Glasgow, Scotland

[21] Appl. No.: 437,323

[22] Filed: Nov. 17, 1989

Related U.S. Application Data

[63] Continuation of Ser. No. 317,130, Mar. 1, 1989, abandoned, which is a continuation of Ser. No. 183,285, Apr. 11, 1988, abandoned, which is a continuation of Ser. No. 927,640, filed as PCT GB86/00056 on Jan. 31, 1986, published as WO86/04497 on Aug. 14, 1986, abandoned.

[30] Foreign Application Priority Data

Jan. 31, 1985 [GB] United Kingdom ................ 8502443

[51] Int. Cl.$^5$ ............................................. A61B 5/0205
[52] U.S. Cl. ..................................... 128/671; 128/670; 128/721
[58] Field of Search ............... 128/670, 671, 695, 696, 128/700, 716, 721, 774, 782

[56] References Cited

U.S. PATENT DOCUMENTS

| | | | |
|---|---|---|---|
| 2,792,828 | 5/1957 | Engeldner | 128/718 |
| 3,268,845 | 8/1966 | Whitmore | 128/721 |
| 3,483,861 | 12/1969 | Tiep | 128/721 |
| 3,510,765 | 5/1970 | Baessler | 128/696 |
| 3,572,316 | 3/1971 | Vogelman et al. | 128/671 |
| 3,587,562 | 6/1971 | Williams | 128/671 |
| 3,742,936 | 7/1973 | Blanie et al. | 128/713 |
| 3,782,368 | 1/1974 | Reibold | 128/721 |
| 3,818,900 | 6/1974 | Nickel | 128/671 |
| 3,820,529 | 6/1974 | Gause et al. | 128/782 |
| 3,830,228 | 8/1974 | Foner | 128/696 |
| 3,976,600 | 8/1976 | Meyer | 338/13 |
| 4,033,332 | 7/1977 | Hardway et al. | 128/722 |
| 4,063,551 | 12/1977 | Sweeny | 128/690 |
| 4,145,317 | 3/1979 | Sado et al. | 338/114 |
| 4,302,361 | 11/1981 | Kotani et al. | 338/114 |
| 4,305,400 | 12/1981 | Logan | 128/670 |
| 4,312,358 | 1/1982 | Barney | 128/670 |
| 4,338,950 | 7/1982 | Barlow, Jr. et al. | 128/782 |
| 4,357,266 | 11/1982 | Sado et al. | 338/114 |
| 4,367,752 | 1/1983 | Jimenez et al. | 128/782 |
| 4,566,461 | 1/1986 | Lubell et al. | 128/700 |

FOREIGN PATENT DOCUMENTS

| | | | |
|---|---|---|---|
| 0117330 | 9/1984 | European Pat. Off. | |
| 2328834 | 12/1973 | Fed. Rep. of Germany | 128/696 |
| 2348582 | 4/1974 | Fed. Rep. of Germany | 128/671 |
| 0751395 | 9/1980 | U.S.S.R. | 128/716 |

OTHER PUBLICATIONS

Skutt et al., "A Multichannel Telemetry System for Use in Exercise Physiology", IEEE Transactions on Biomedical Engineering, vol. BME-17, No. 4, pp. 339-348, Oct. 1970.

Primary Examiner—Lee S. Cohen
Assistant Examiner—Kennedy J. Schaetzle
Attorney, Agent, or Firm—Pennie & Edmonds

[57] ABSTRACT

An apparatus is disclosed for monitoring physiological parameters comprising a harness adapted to be worn by a human being and electrical circuitry connected to the harness for calculating physiological parameters in accordance with predetermined algorithms. The harness includes a band which extends around a trunk portion of the human being. The band comprises an inelastic portion and an elastic portion. The elastic portion incorporates an electro-conductive elastomeric means which has a resistance value which changes as a function of elongation of the elastic portion. The electrical circuitry connected to the elastomeric element calculates and displays various physiological parameters.

5 Claims, 10 Drawing Sheets

Relationship between peak height and $O_2$ consumed (L): FEMALES.

APPARATUS FOR MONITORING PHYSIOLOGICAL PARAMETERS

This is a continuation of application Ser. No. 07/317,130, filed Mar. 1, 1989, now abandoned, which is a continuation of No. 07/183,285, filed; Apr. 11, 1988, now abandoned, which is a continuation of No. 06/927,640, filed as Pct GB86/00056 on Jan. 31, 1986, published as WO86/04497 on Aug. 14, 1986, now abandoned.

SUMMARY OF THE INVENTION

This invention relates to apparatus for monitoring physiological parameters in human beings.

According to the present invention there is provided apparatus for monitoring physiological parameters in human beings, said apparatus comprising a harness adapted to be worn on the upper body of a human being and incorporating a circumferential band for extending around the trunk portion between the thorax and the abdomen of said upper body, said band comprising a substantial inelastic portion circumferentially conjoined with an elastic portion, said elastic portion incorporating an electro-conductive elastomeric element having an electrical resistance value which changes as a function of elongation of said elastic portion, and means electrically connected to said element for analyzing changes in said resistance value arising from changes in volume of said trunk portion and establishing physiological parameters therefrom in accordance with predetermined algorithms.

Preferably said electro-conductive elastomeric element comprises a silicone polymer gum loaded with graphitic carbon particles in the presence of an unsaturated oil having a carbon chain length of at least 16 and a high degree of mesogenicity, together with crosslinking and curing agents. Preferably the unsaturated oil is a fixed vegetable oil such as arachis oil. Alternatively, the oil may be di-oleyl oxalate.

The preferred formulation of the elastomeric element is 100 g silicone polymer gum (C2501) (as sold by J-Sil Ltd.), 70 g graphitic carbon (having a particle size of the order of 50 microns or less), 5 g crosslinker (Silester O.S.), 2 g curing agent (di-butyl tindilaurate) and 20 g arachis oil. It is preferred that in preparing this formulation the constituents be admixed with a volatile additive in which the oil and gum dissolve and/or disperse miscibly for the purpose of enhancing homogeneity of the mixture. The preferred such additive is toluene in a quantity of the order of 100 ml.

Preferably said analyzing means comprises data entry means for entering personal characteristics of the human being whose physiological parameters are being monitored, such characteristics including sex gender and quantitative data of height and weight. Conveniently said data entry means comprises an alphanumeric keyboard.

Preferably said data entry means comprises mode conditioning means for establishing the mode of operation of the analyzing means.

Preferably the analyzing means comprises first signal conditioning means for conditioning the electrical signal waveform received from the elastomeric element, said conditioning means comprising means for analogue smoothing the signal by elimination of its high frequency modulation.

Preferably the analyzing means further comprises second signal conditioning means for effecting a frequency analysis of the signal received from the elastomeric element in order to identify, after removal of noise components, its three principal frequencies. Conveniently noise is eliminated by way of a highpass filter. In this connection it is to be understood that the signal emanating from the elastomeric element principally comprises a first frequency component of large amplitude which represents the breathing rate of the human being, a second frequency component of medium amplitude which represents the rate of total body movement of the human, and a third frequency component of lesser amplitude than the first and second frequency components which represents the heart rate of the human, these three frequency components being of substantially greater amplitude than signal noise and their harmonics.

It is preferred that the analyzing means comprises a frequency comparator coupled to receive the signals generated by the first and second signal conditioning means and means for identifying the breathing rate frequency component provided by the second signal conditioning means by that provided by the first signal conditioning means. Subtraction means is provided to remove the matched breathing rate signal from the signal provided by the second signal conditioning means.

Preferably also the analyzing means further comprises gating means to which the output of the subtraction means is delivered whereby the remaining two frequency components of the signal from the subtraction means are separated on an amplitude discrimination basis.

Preferably also the analyzing means comprises a first calculation means for evaluating body surface area of the human being according to a predetermined algorithm; second calculation means for evaluating calories consumed by the human being in unit time on the basis of a second predetermined algorithm; and third calculation means for evaluating a fitness factor according to a third predetermined algorithm.

The first algorithm is a function of height and weight of the human being and is in accordance with the formula defined by E.F. Dubois in a publication entitled "Basal Metabolism in Health and Disease" published in 1927.

The second predetermined algorithm is a function of the peak value of the breathing rate signal identified by the first signal conditioning means, the sex gender of the human being and the standard respiratory quotient.

The third predetermined algorithm is a function of the metabolic quotient derived from the apparatus in the absence of the human being effecting aerobic exercises, i.e. the basal metabolic quotient; the metabolic quotient derived from the apparatus when the human being is undertaking aerobic exercises; the recovery time established by the apparatus following completion of aerobic exercises for the breathing rate to return to its basal level; the recovery time for the heart rate to return to its basal level; and the total energy consumed over the exercise period.

BRIEF DESCRIPTION OF THE DRAWINGS

An embodiment of the present invention will now be described by way of example with reference to the accompanying drawings, in which.

DETAILED DESCRIPTION OF THE INVENTION

Figure 1:
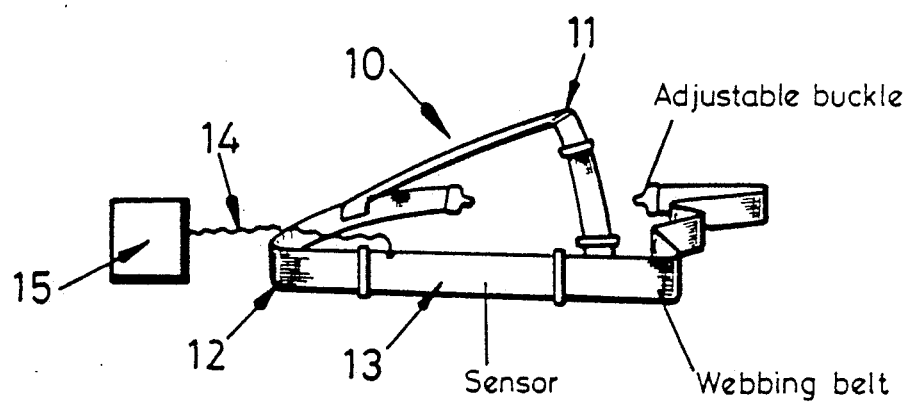
FIG. 1 pictorially illustrates apparatus according to the present invention.
Figure 2:
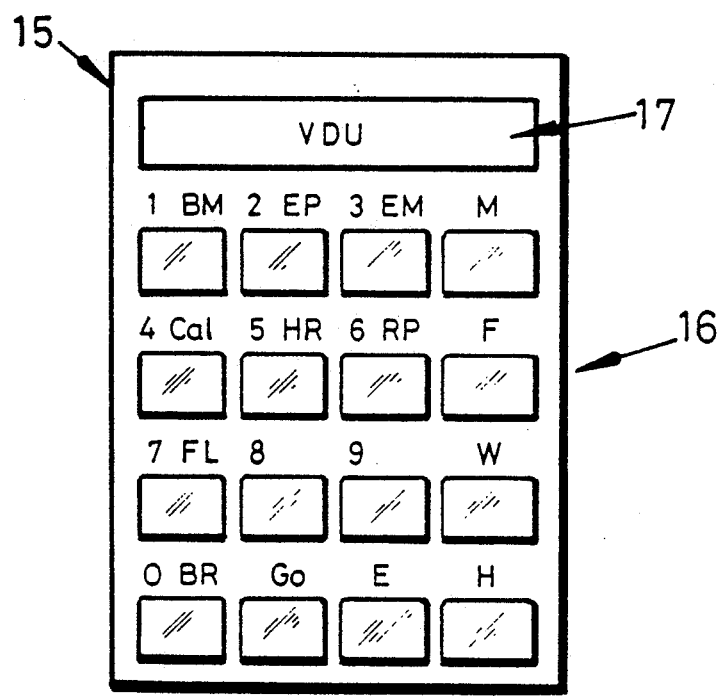
FIG. 2 illustrates a component of FIG. 1 in greater detail.

As is shown in FIGS. 1 and 2 the apparatus comprises a harness 10 incorporating a shoulder strap arrangement 11 and a band 12 capable of extending around the trunk portion of a human being whose physiological parameters are to be monitored. The band 12 comprises a substantially inelastic portion accounting for about 70% of the length of the band 12 and which is conjoined circumferentially with an elastic portion 13 which accounts for the remainder of the length of the band. The elastic portion is situated within the band 12 so as to be located in the region of the thorax when the harness 10 is fitted to the human being so that the portion 13 is freed from sensing movements imposed by the arms brushing against portion 13 when the human being effects aerobic exercises such as running, jogging, weight lifting and the like.

The portion 13 functions as a sensor and is preferably formed by a layer of electro-conductive elastomeric material having the composition previously referred to sandwiched between elastomeric non-conductive layers externally sheathed by an elastomeric sleeve. The sleeve is preferably made of H.T.V. silicone polymer while the non-conductive elastomeric layers are preferably made of R.T.V. Silicone polymer. The various layers of portion 13 are bonded together to exclude air from the interior thereof and electrical leads 14 extend from the electro-conductive element within portion 13 to a box-like housing 15 which is adapted to be carried by the human being. Housing 15 for example may be releasably secured to shoulder strap arrangement 11.

Housing 15 incorporates an alphanumeric keyboard 16 whereby personal and physical characteristics of the pertaining human being may be entered into electronic circuitry contained within housing 15 which circuitry is adapted to process the signals emanating from portion 13 as will be explained.

The electrical circuitry within housing 15 is preferably formed from CMOS Components driven from a regulated voltage source powered by a dry battery releasably secured to housing 15. Furthermore, housing 15 incorporates a visual display unit 17 whereby data being entered via the keyboard 16 can be checked visually and output data generated by the electronic circuitry can be displayed to the relevant human being.

It will be appreciated from the foregoing that the apparatus of the embodiment described is wholly portable, but in an alternative embodiment which is intended for use in gymnasiums and other establishments where aerobic exercises are effected at a substantially static location the housing 15 may be console mounted.

Figure 3:
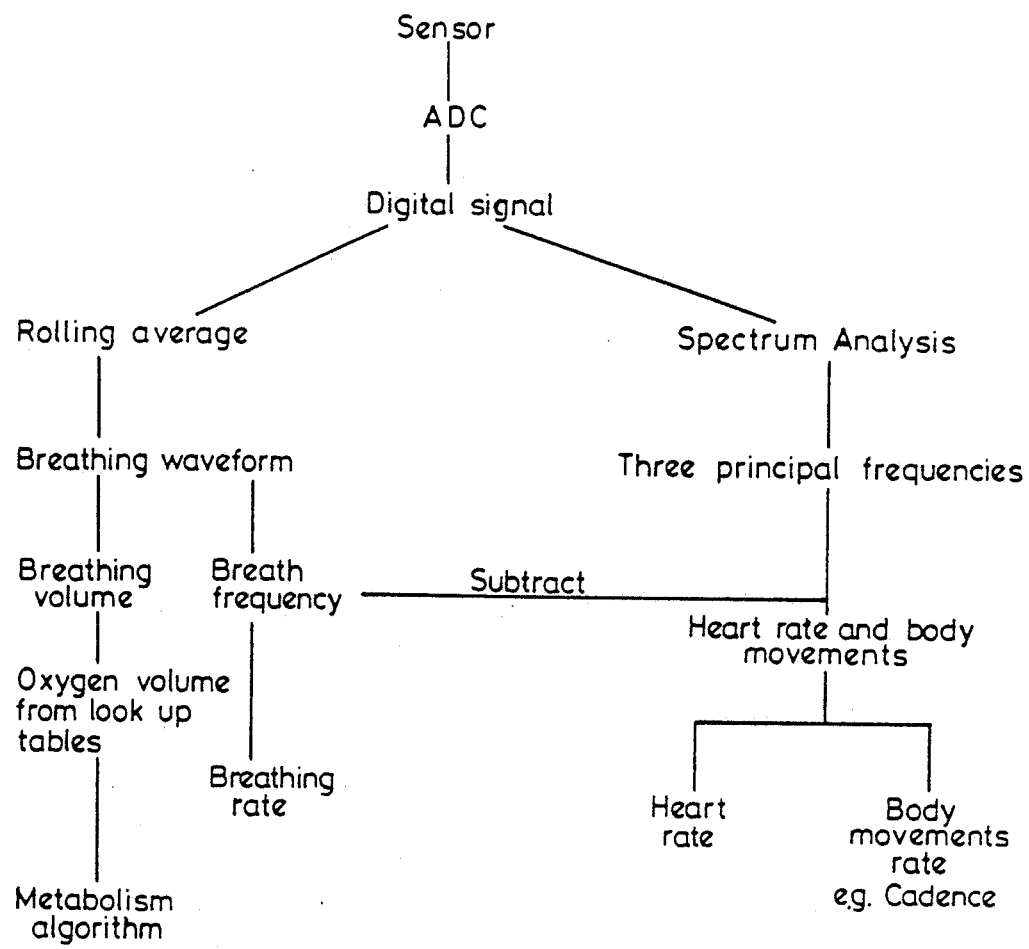
FIG. 3 is a flow chart illustrating the operation of the FIG. 2 component.
Figure 4:
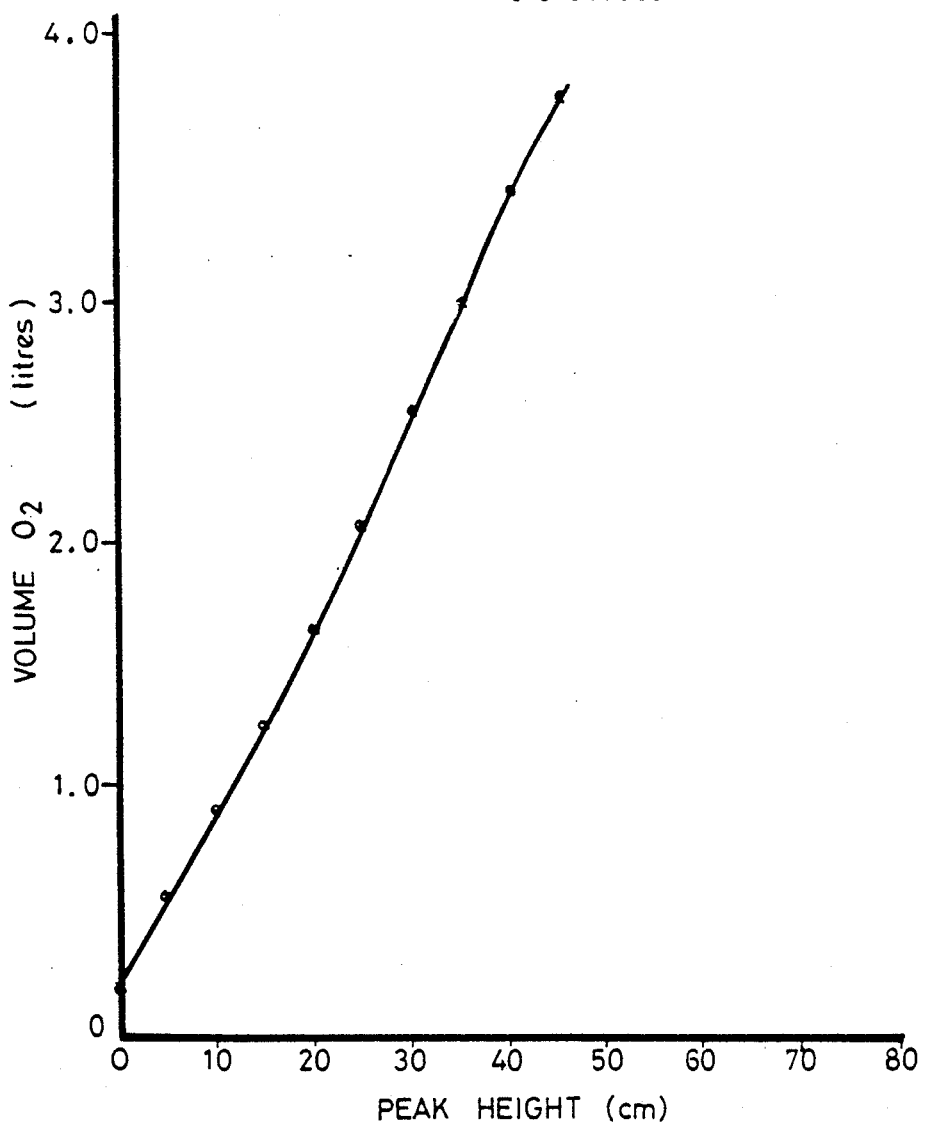
FIGS. 4 and 5 illustrate calibration curves utilized in the FIG. 2 component.
Figure 5:
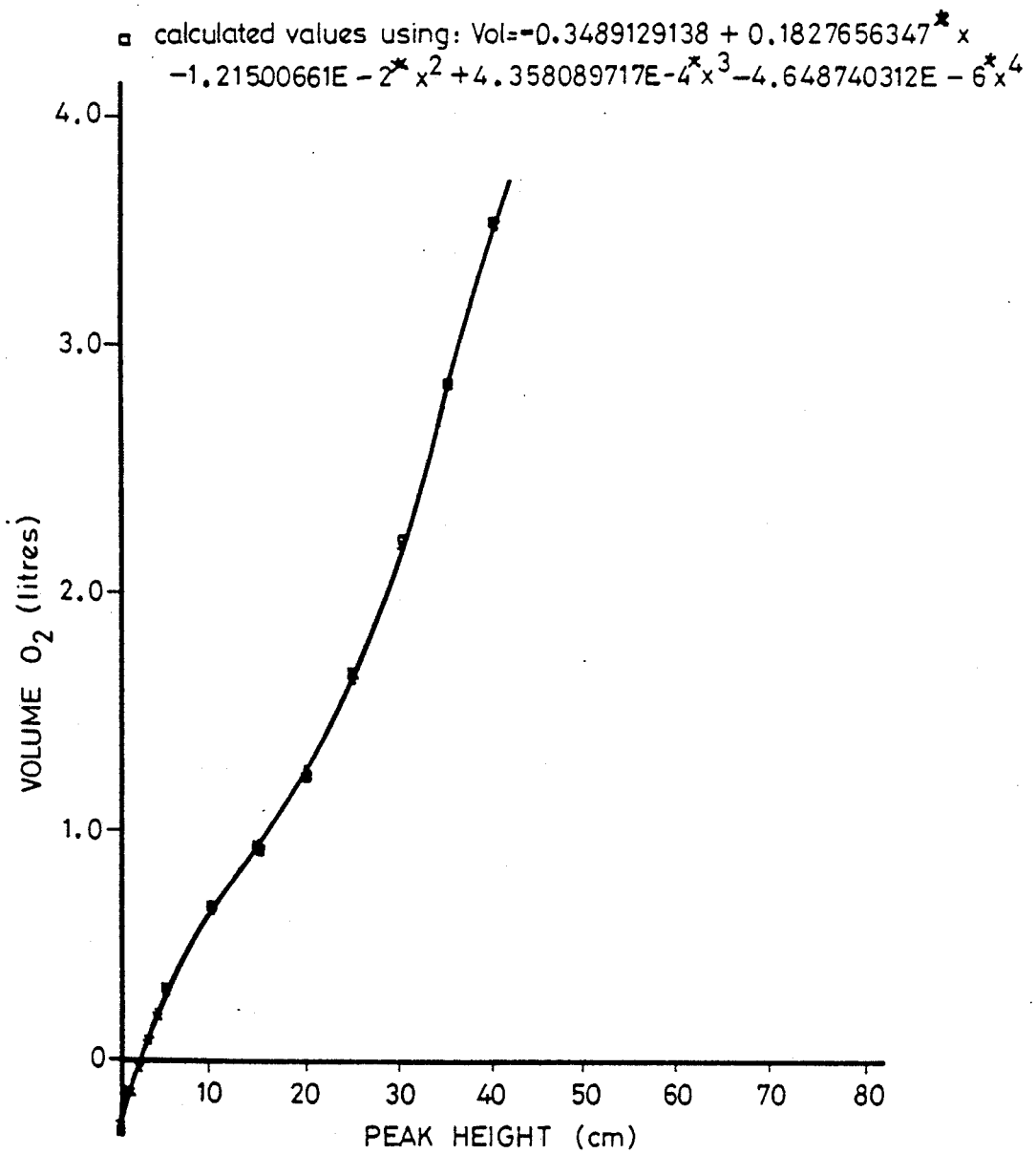

Elastomeric portion 13 functions as a thoraco-abdominal-plethysmographic sensor measuring volumetric changes of the human trunk which primarily are caused by respiratory movements and heart beats. Accordingly the signal from the sensor 13 is delivered to the electronic circuitry within housing 15 where it is processed by components functioning in the manner set forth in the flow chart of FIG. 3 as has been explained above. Thus the sensor signal is first analoge to digital converted and conditioned by a first conditioning circuit to establish a breathing waveform the peak value of which correlates to a breathing volume in accordance with the graph of FIG. 4 for males and FIG. 5 for females. The graph of FIG. 4 represents the polynomial equation $$\begin{aligned}\text{Volume} = \; & 0.01959294747 \\ & +7.87942922 \times 10^{-2}\,p \\ & -1.535787013 \times 10^{-3}\,p^2 \\ & +7.58847716 \times 10^{-5}\,p^3 \\ & -0.313979237 \times 10^{-7}\,p^4\end{aligned}$$

where P represents the peak height value of the breathing waveform.

$$\begin{aligned}\text{Volume} = \; & -0.3489129138 \\ & +0.18276566346P \\ & -1.21500661 \times 10^{-2}\,p^2 \\ & +4.358089717 \times 10^{-4}\,p^3 \\ & -4.648740312 \times 10^{-6}\,p^4\end{aligned}$$

The circuitry also calculates the body surface area of the human from the formula $$\text{Area (m}^2\text{)} = W^{0.425} \times H^{0.725} \times 0.07184$$

where W = weight in Kg and H = height in metres and further calculates Metabolic Rate (or Quotient) from the formula $$MQ = \frac{\text{Vol.} \times 0.23865 \times 60 \times \text{Respiration Rate}}{\text{Body Surface Area}}$$

Respiration Rate is calculated by the electronic circuitry, by identifying the nadir points of the signal provided by the first signal conditioning means and measuring the time intervals between such detected nadirs.

A second signal conditioning circuit operating in parallel with the first signal conditioning circuit effects a spectral analysis of the sensor signal so as to identify its three principal-amplitude frequencies. Breathing rate (or respiration rate) which is uniquely identified via the first signal conditioning circuit is removed from the three spectrally identified principal frequencies so as to leave heart rate and body movement rate frequencies which are then separated on an amplitude discrimination basis.

The electronic circuitry further calculates a fitness level factor from the formula $$\text{Fitness Level Factor} = \frac{E100}{N} \times \frac{1}{B} \times \frac{1}{H} \times f(TC)$$

where

E maximum metabolic quotient during exercising

N = metabolic quotient basal (i.e. in the absence of exercising)

B = time for breathing rate on termination of exercising to recover to basal level H = time for heart rate on termination of exercising to recover to basal level TC = total energy (calories) consumed during exercising TC is calcuated as the mean value of metabolic quotient during exercising multiplied by the duration of exercising multiplied by Body Surface Area.

Figure 6:
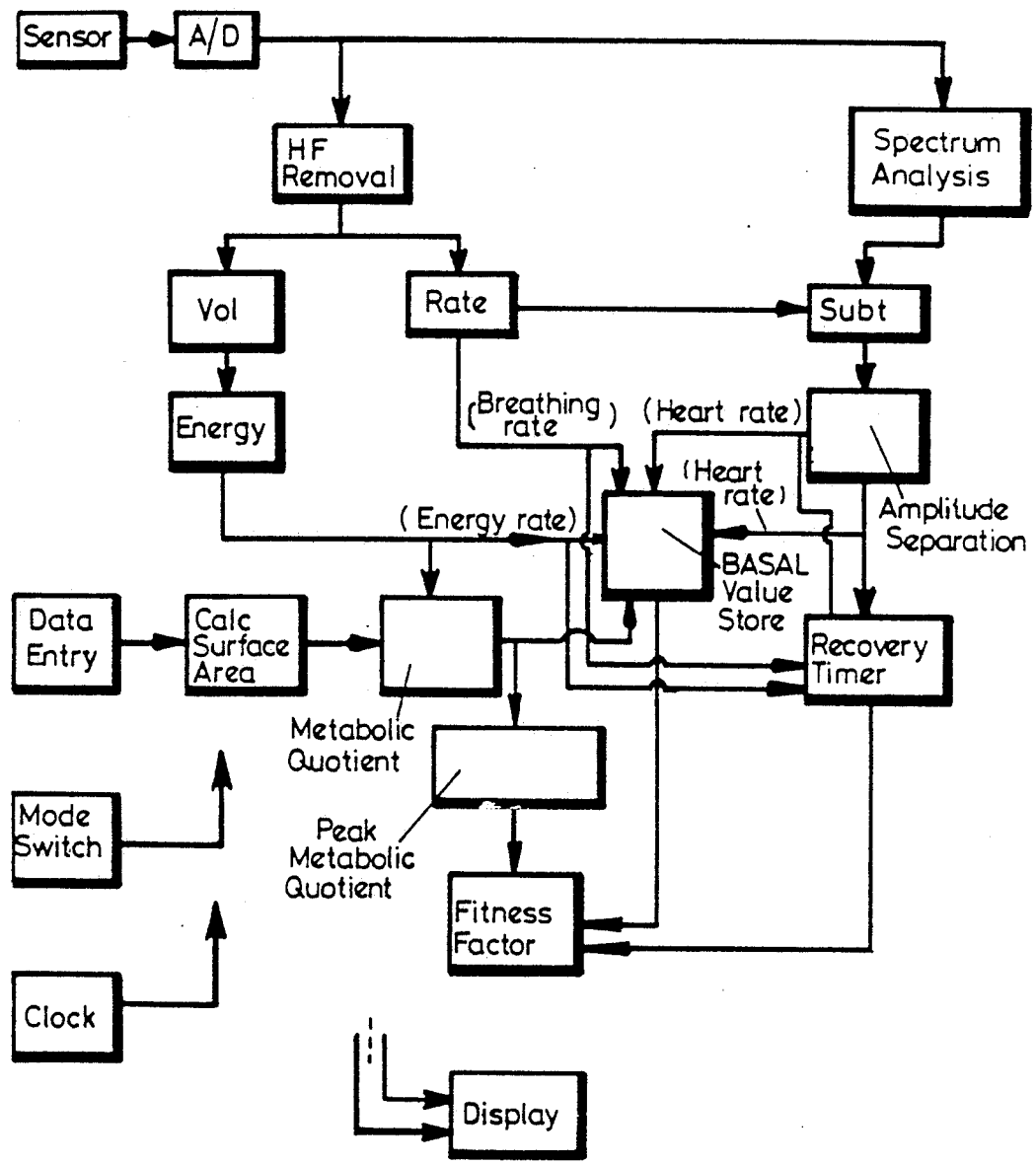
FIG. 6 is a block diagram of the circuitry within the FIG. 2 component.
Figure 7:
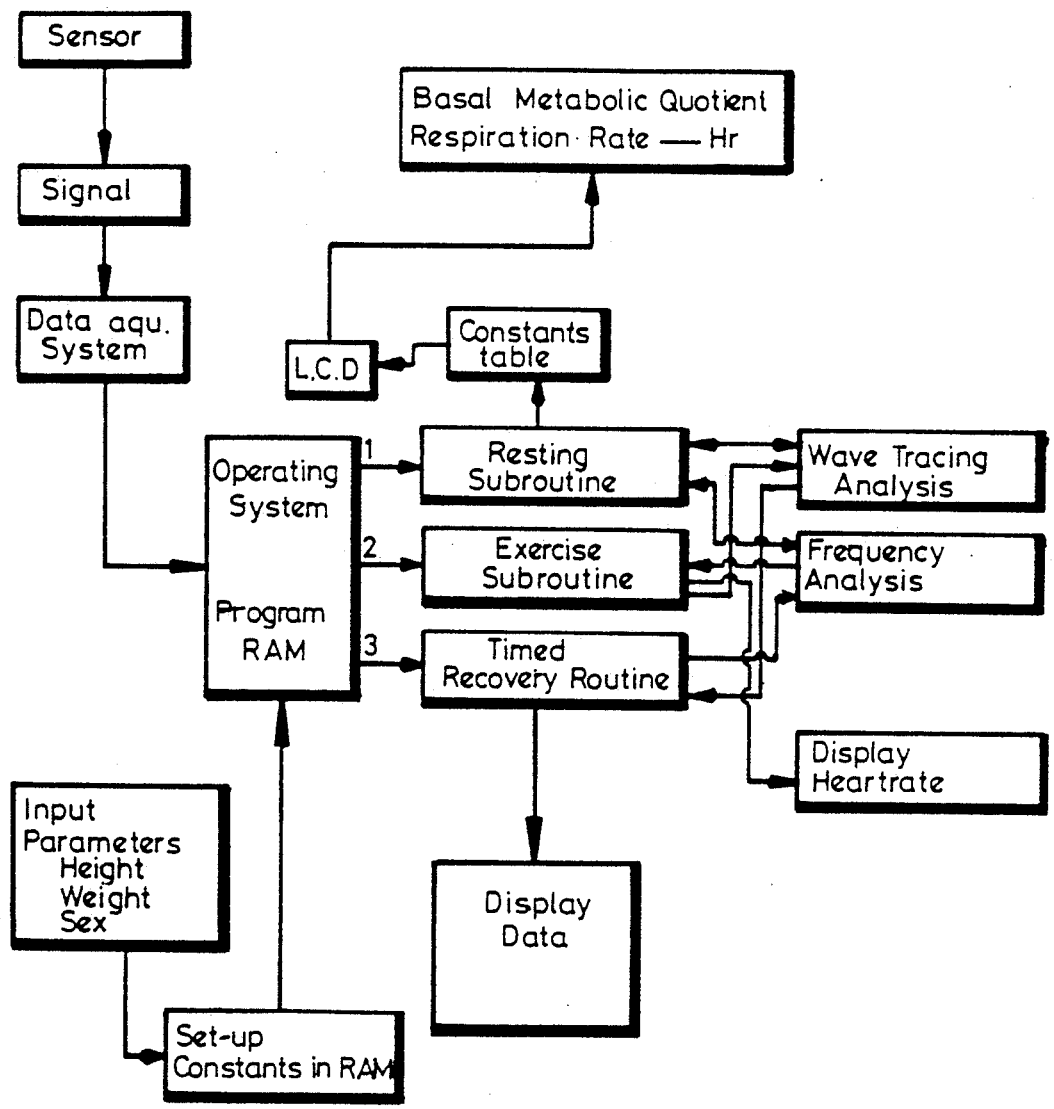
FIG. 7 is a block diagram of an alternative software implementation of the operation of the FIG. 2 component.
Figure 8:
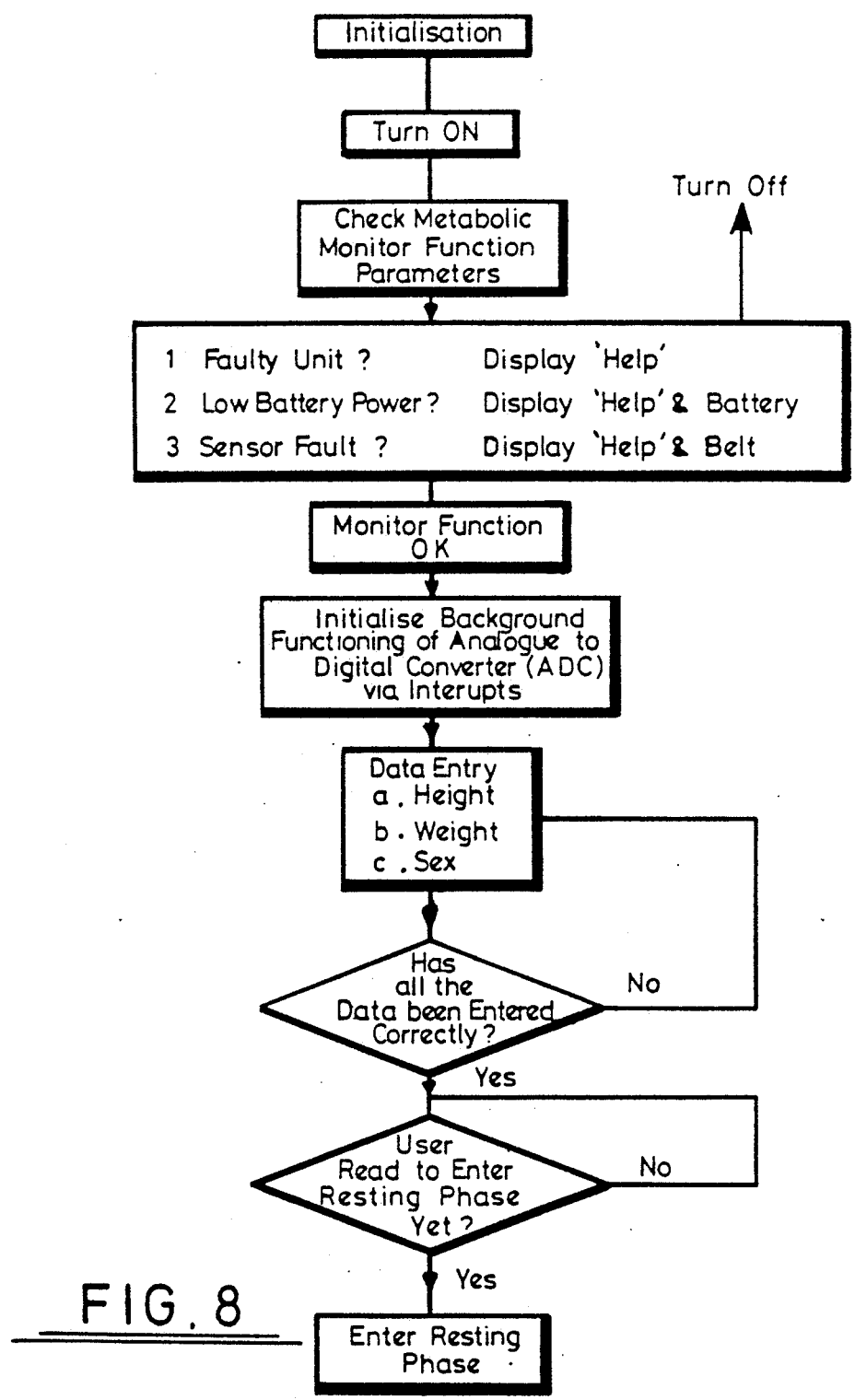
FIGS. 8–11 are flow charts illustrating implementation of the FIG. 7 block diagram.
Figure 9:
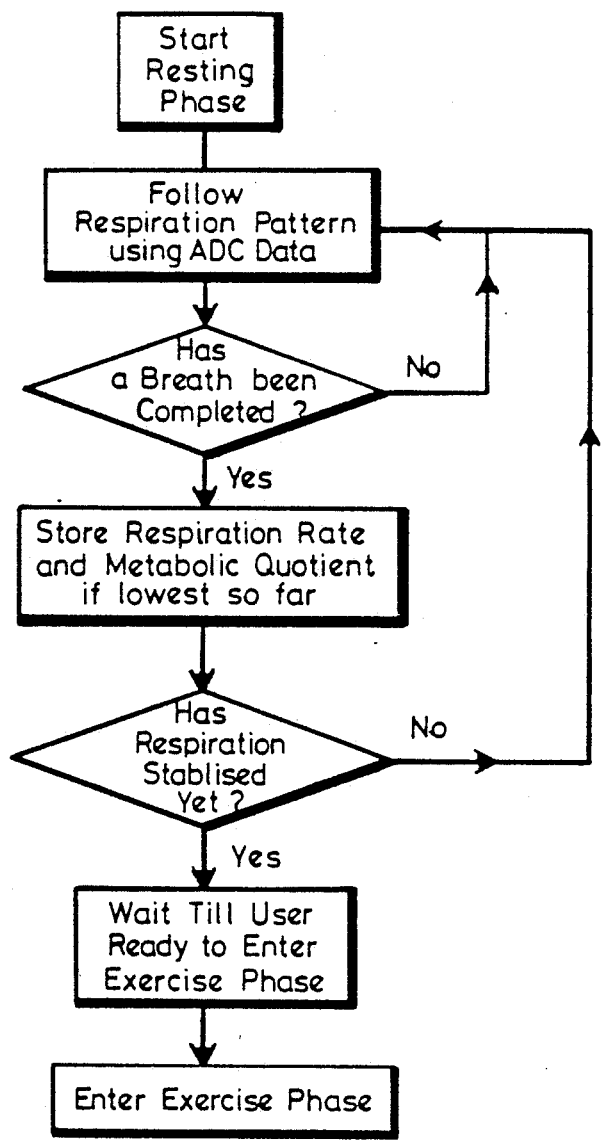
Figure 10:
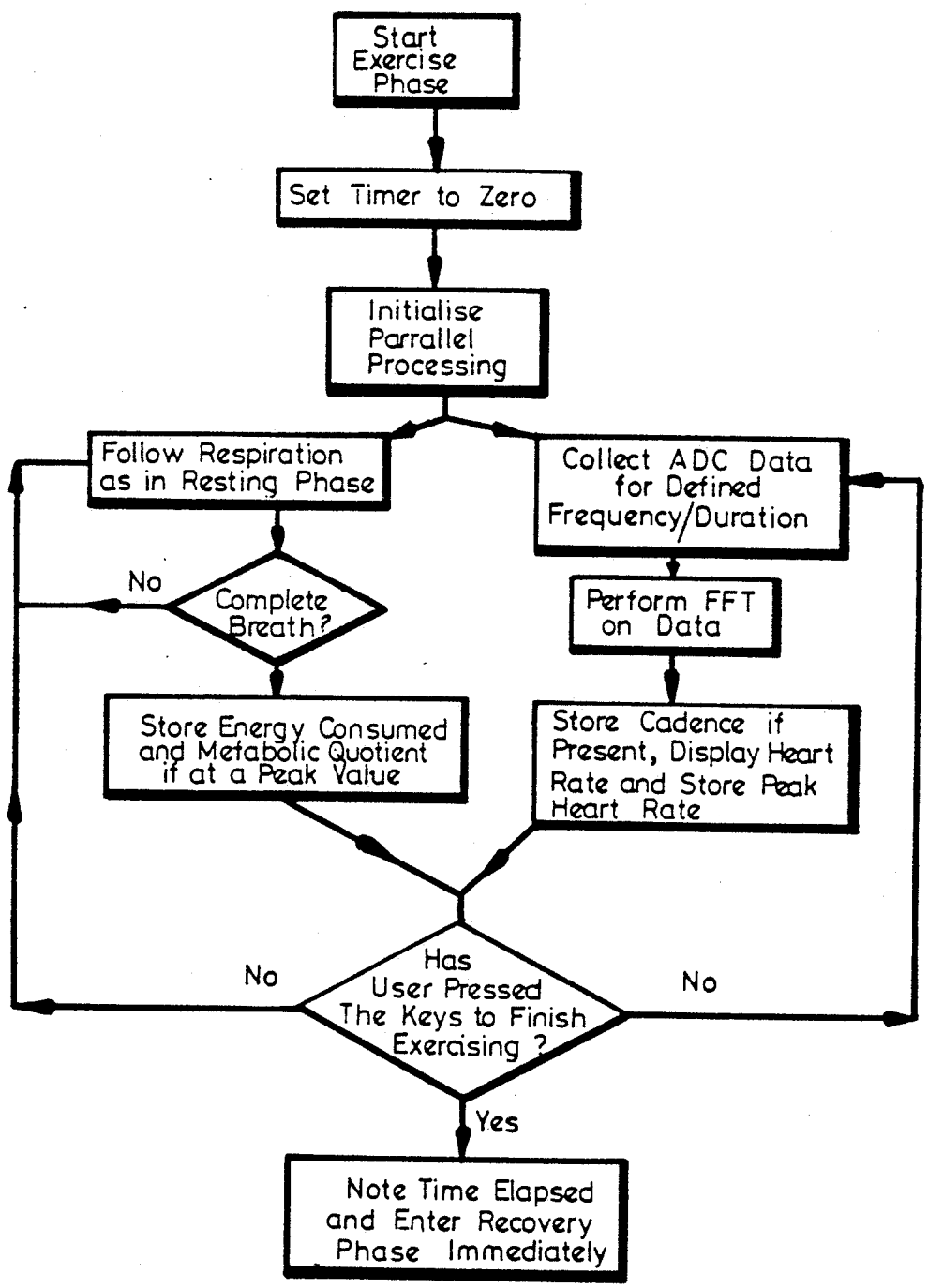
Figure 11:
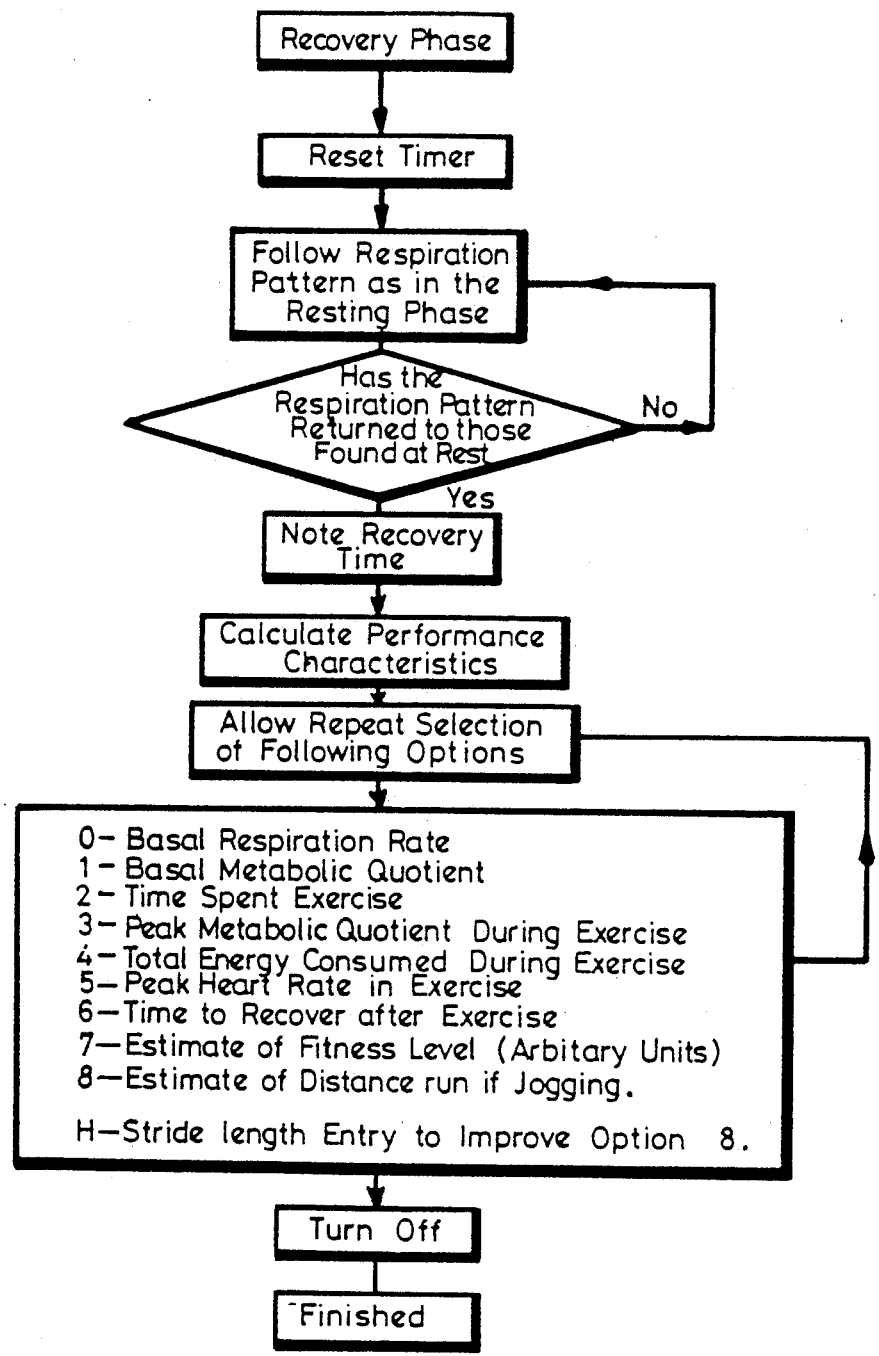

FIG. 6 illustrates a block diagram of the circuitry contained within housing 15 in a discrete component implementation whereas FIG. 7 is a corresponding block diagram of a software implementation. Typical constituents used in the FIG. 7 diagram are a crystal oscillator to provide the clock signal to the main processor; a 74138 integrated circuit for switching off and on other integrated circuits as required; 2764 EPROM's for storing the main software program; a 6116 RAM for temporary storage of data that is changed from time to time; a 6502 central processor for obeying the commands generated by the programs of the 2764 ICs and controlling all other ICs accordingly, being responsible for all calculations, storage and retrieval of data from the 6116 and for operating the visual display unit (LCD) via a 6522 interface The 6522 interface drives the LCD display and accepts data from the keyboard to input data to the 6502 with the aid of a 7403 interfacing half the lines from the keyboard to the 6522. A 4528 is provided for initiating (resetting) the 6502 and 6522 when power is applied. 7400/U6 and 7400/U5 IC gates are provided to control ICs which cannot be directly controlled by the 74138. A voltage regulator in the form of a 78LO5A is provided.

The previously described apparatus is used as follows: The sensor is placed around the chest and abdomen, at a slight tension, not hindering breathing in any way and stretched to about 110% of its original length. The sensor should be about 1-2 inches below the breast bone (sternum). Once the sensor is properly in position, the user should breathe deeply at least three times to check that the sensor is not interfering with breathing.

The electronic circuitry is started by plugging the sensor into the instrument case and switching on the power supply. This should result in '0' being displayed at the extreme left position of the display.

If nothing happens then a battery change should be tried, else the unit is faulty.

If '?HELP' is displayed this could mean one of the following:

(a) the sensor is not plugged in properly (b) the sensor is faulty/too tight. in this case "BELT" will flash on the display.

(c) there is insufficient power for full function: in this case "BATTERY" will flash on the display.

Personal and physical details may be entered in any order, and as many times as it takes to get it right.

To enter sex, the user must press either the 'M' key for male or the 'F' key for female. "SEX" will flash plus a flashing "0" will appear on the display for females, and a flashing "1" for males.

To enter weight, the user must press the 'W' key "POUNDS" and "?" will then appear on the display and the users weight in pounds should now be entered. After doing so the key marked 'E' must be pressed to enter the data, the display will not now show the "? ".

To enter height, the same sequence as for weight is followed, but the 'H' key is used and height in feet and inches is entered. "FEET" plus "?" or "INCHES" plus "?" will be displayed. After entry the "?" will be no longer displayed.

If an attempt is made to do anything further before all these parameters have been entered the "?" will keep flashing, with the omitted parameters also flashing. Once all are entered the circuitry is ready to establish the basal metabolic rate.

In order to determine the basal values of the variables the 'GO' key is pressed followed quickly by the 'E' key. Here the user must relax. A flashing '0' will then appear on the display. After about 90 seconds a number will appear. This is the current determination of the users basal metabolic quotient. Basal metabolic quotient is an approximation of basal metabolic rate.

Now the user can enter the exercise phase. This is done by pressing 'GO' and 'E' again in quick succession. The user should now start exercising. Although the user should start exercising as soon as 'GO' and 'E' are pressed he can delay pressing these for as long as he wishes and thus only enter exercise phase when he is completely ready.

While the user is exercising, a heart shape will be displayed followed by the users heart rate.

When the user has finished exercising, he should immediately press 'GO' then 'E' so as to cause the circuitry to enter the recovery phase. A flashing '0' will then appear on the display as the circuitry follows the user's respiration until resting levels are reestablished.

When the display clears, data is available on the user's performance and this is shown by the "?" and "SELECT KEY" appearing on the display.

The keys now act as function keys and will display the following details of the user's performance:

| KEY | DATUM | UNITS USED |
|---|---|---|
| 0 | Resting breathing rate | per minute |
| 1 | Normal basal metabolic quotient | Kcals/M$^2$/Hr |
| 2 | Exercise duration | HH:MM:SS |
| 3 | Exercise metabolic quotient | Kcals/M$^2$/Hr |
| 4 | Calories consumed in exercise | Kcalories |
| 5 | Peak heart rate during exercise | per minute |
| 6 | Recovery time | HH:MM:SS |
| 7 | Fitness level | arbitary |
| 8 | Distance covered (assuming jogging) | Kilometers |

Pressing 'GO' and 'E' at any stage will always move the circuitry onto the next phase. If this is done too soon, insufficient data will have been available causing the apparatus to fail or to produce some erroneous values.

Flow charts of these procedures are illustrated in FIGS. 8 to 11.

The embodiment which has been described utilizes sensor 13 carefully positioned on the trunk of the human being so that the heart rate signal which is sensed is of sufficiently significant value as to be discriminated over attendant electrical noise levels. Because sensor 13 represents only about 30% or less of the circumferential length of the band 12 there is an amplification of the thorax movements so that a relatively small movement in the inelastic portion of the belt 12 appears as a relatively large movement in the sensor 13. Accordingly it is not necessary to filter the sensor signal on lead 14 nor to amplify that signal.

The signal appearing on lead 14 is of course an analog signal and because in accordance with modern techniques the electrical circuitry within housing 15 functions on a digital basis the signal from the sensor is initially analog-to-digital converted at a sampling rate which is at east four times the anticipated maximum heart beat rate. In this way all important characteristics of the sensor signal are retained in the digitized version thereof. A convenient arrangement for removing the high frequency components of the sensor signal is to effect a rolling average of four digital samples so that the average sample amplitude of four digital samples is calculated prior to the presence of a next occurring digital sample at which point the average is rolled over to that next occurring digital sample and its immediately three preceding digital samples and so on.

Insofar as the apparatus which has been described monitors physiological parameters in human beings the apparatus may be used in the fields of medicine, such as rehabilitation, physical fitness training such as gymnasium tests, jogging, running, cycling, weight lifting and any other physical exertion which involves anaerobic activity (i.e. where the breath is held for longer than normal in undertaking the exercises), and dieting. It will be appreciated in this connection that the physical fitness level previously referred to is not in itself an absolute value applicable at large, but is relative to the particular type of body function undertaken, i.e. gymnasium tests etc. provide a different fitness level factor from dieting tests.

What is claimed is:

1. Apparatus for monitoring physiological parameters in human beings, said apparatus comprising a harness adapted to be worn on the upper body of a human being and incorporating a single circumferential band for extending around the truck portion between the thorax and the abdomen of said upper body, said band comprising a substantially inelastic portion circumferentially conjoined with an elastic portion, said elastic portion incorporating an electroconductive elastomeric means having an electrical resistance value which changes as a function of elongation of said elastic portion, and analyzing means electrically connected to said elastomeric means for analyzing changes in said resistance value arising from changes in volume of said trunk portion and establishing physiological parameters therefrom in accordance with predetermined algorithms, wherein said analyzing means comprises data entry means for entering personal characteristics of the human being whose physiological parameters are being monitored, such characteristics including sex gender and quantitative data of height and weight, and the analyzing means further comprises first signal conditioning means for conditioning the electrical signal waveform received form the elastomeric means to establish a breathing waveform, said first signal conditioning means comprising means for analogue smoothing of the signal by elimination of its high frequency content.

2. Apparatus as claimed in claim 1, wherein the analyzing means further comprises second signal conditioning means for effecting a frequency analysis of the signal received from the elastomeric means in order to identify, after removal of noise components, its three principal frequencies, frequency comparator means coupled to receive the signals generated by the first and second signal conditioning means for identifying the breathing rate frequency component provided by the second signal conditioning means by comparison with the breathing waveform provided by the first signal conditioning means, said frequency comparator means including substraction means to remove the matched breathing rate signal from the signal provided by the second signal conditioning means, and amplitude-discrimination gating means to which the output of the subtraction means is delivered whereby the remaining two frequency components of the signal from the subtraction means are separated on an amplitude discrimination basis.

3. Apparatus as claimed in claim 1, wherein the analyzing means comprises a first calculation means for evaluating body surface area of the human being according to a first predetermined algorithm; second calculation means for evaluating calories consumed by the human being in unit time on the basis of a second predetermined algorithm; and third calculation means for evaluating a fitness factor according to a third predetermined algorithm.

4. Apparatus as claimed in claim 2, wherein the analyzing means comprises a first calculation means for evaluating body surface area of the human being according to a first predetermined algorithm; second calculation means for evaluating calories consumed by the human being in unit time on the basis of a second predetermined algorithm; and third calculation means for evaluating a fitness factor according to a third predetermined algorithm.

5. Apparatus as claimed in claim 4, wherein the first algorithm is a function of height and weight of the human being and is in accordance with a known formula, the second predetermined algorithm is a function of the peak value of the breathing rate signal identified by the first signal conditioning means, the sex gender of the human being and the standard respiratory quotient, and the third predetermined algorithm is a function of the basal methabolic quotient derived by the analyzing means in the absence of the human being effecting aerobic activity, the metabolic quotient derived by the analyzing means when the human being is undertaking aerobic activity, the recovery time established by the analyzing means following completion of aerobic activity for the breathing rate to return to its basal level, the recovery time for the heart rate to return to its basal level, and the total energy consumed over the activity period.

* * * * *